(12) United States Patent
Son et al.

(10) Patent No.: US 7,294,415 B2
(45) Date of Patent: Nov. 13, 2007

(54) ORGANOMETALLIC COMPLEX AND ORGANIC ELECTROLUMINESCENT DEVICE EMPLOYING THE SAME

(75) Inventors: Hae-Jung Son, Seoul (KR); Eun-Sil Han, Daejeon-si (KR); Jong-Hyoup Lee, Seoul (KR); Lyong-Sun Pu, Suwon-si (KR); Seok Chang, Daejeon-si (KR); Yi-Yeol Lyu, Daejeon-si (KR); Das Rupasree Ragini, Suwon-si (KR)

(73) Assignee: Samsung SDI Co., Ltd., Suwon-si, Gyeonggi-do (KR)

( * ) Notice: Subject to any disclaimer, the term of this patent is extended or adjusted under 35 U.S.C. 154(b) by 404 days.

(21) Appl. No.: 10/875,651

(22) Filed: Jun. 25, 2004

(65) Prior Publication Data

US 2004/0265633 A1 Dec. 30, 2004

(30) Foreign Application Priority Data

Jun. 26, 2003 (KR) .................... 10-2003-0042129

(51) Int. Cl.
*H01L 51/54* (2006.01)
*C09K 11/06* (2006.01)

(52) U.S. Cl. .................. 428/690; 428/917; 313/504; 257/E51.044; 546/2; 546/4; 546/5; 556/136; 556/137

(58) Field of Classification Search ............... None
See application file for complete search history.

(56) References Cited

U.S. PATENT DOCUMENTS

| | | | |
|---|---|---|---|
| 6,869,693 B2 * | 3/2005 | Fryd et al. | 428/690 |
| 2002/0048689 A1 | 4/2002 | Igarashi et al. | 428/690 |
| 2002/0125818 A1 * | 9/2002 | Sato et al. | 313/504 |
| 2002/0190250 A1 * | 12/2002 | Grushin et al. | 257/40 |

FOREIGN PATENT DOCUMENTS

WO    WO 2005/118606 A1 * 12/2005

OTHER PUBLICATIONS

Grant & Hackh's Chemical Dictionary, 5th ed., 1987, McGraw-Hill, Inc., p. 53.*
S. Sprouse et al., "Photophysical Effects of Metal-Carbon σ Bonds in Ortho-Metalated Complexes of Ir(III) and Rh(III)", *J. Am. Chem. Soc.* vol. 106, pp. 6647-6653, American Chemical Society, 1984.
M. A. Baldo et al., "Very high-efficiency green organic light-emitting devices based on electrophosphorescence", Applied Physics Letters, vol. 75, No. 1, pp. 4-6, American Institute of Physics, Jul. 5, 1999.

* cited by examiner

*Primary Examiner*—Marie Yamnitzky
(74) *Attorney, Agent, or Firm*—Robert E. Bushnell, Esq.

(57) ABSTRACT

An organometallic complex which includes a carboxylic acid as an ancillary ligand, and an organic electroluminescent device employing the same. The organometallic complex is useful as a phosphorescence dopant material of an organic electroluminescent device due to its high luminosity in the range of the blue wavelengths.

20 Claims, 3 Drawing Sheets

ORGANOMETALLIC COMPLEX AND ORGANIC ELECTROLUMINESCENT DEVICE EMPLOYING THE SAME

CLAIM OF PRIORITY

This application makes reference to, incorporates the same herein, and claims all benefits accruing under 35 U.S.C. §119 from an application for ORGANOMETALLIC COMPOUND AND ORGANIC ELECTROLUMINESCENT DEVICE EMPLOYING THE SAME, earlier filed in the Korean Intellectual Property Office on Jun. 26, 2003 and there duly assigned Serial No. 2003-42129.

BACKGROUND OF THE INVENTION

1. Field of the Invention

The present invention relates to an organometallic complex and an organic electroluminescent device employing the same, more particularly relates to an organometallic complex having excellent luminescence properties in the range of the blue wavelengths.

2. Description of the Related Art

An organic electroluminescent display (organic EL display) is an active light-emitting display using a fluorescent or a phosphorescent organic compound that emits light in response to the recombination of holes injected from an anode and electrons injected from a cathode in the organic film when an electric current is applied to a thin film (hereinafter referred to as "organic film") composed of the fluorescent or phosphorescent organic compound. Further, since an organic electroluminescent display has various advantages such as light weight, simple structure which can be manufactured in an uncomplicated manufacturing process, a large viewing angle, high brightness, full color, low power consumption, low driving voltage and complete expression of moving picture, the display is very useful in portable electronic devices.

Luminescence of an electroluminescent display is obtained by injecting holes from an anode and electrons from a cathode into a light-emitting layer. The holes and the electrons are recombined in the light emitting layer to form excitons, and emit light with a wavelength corresponding to a band gap when the exciton radiatively decays.

The light emitting layer-forming materials are classified into fluorescent materials using single state excitons and phosphorescent materials using triple state excitons, according to a luminescence mechanism.

The fluorescent material using singlet excitons has been employed in conventional organic electroluminescent devices. In this case, however, three-fourth of the energy produced by the excitons is not used.

When the fluorescent materials are used as luminescent materials, that is, a luminescence process mediated by an exciton in a singlet state is used, the internal quantum efficiency is at most about 25%. Furthermore, the actual external quantum efficiency is at most 5% since an extraction efficiency of light is affected by the refractive index of substrate materials. There are such limitations as long as fluorescence of singlet state excitons is used. Thus, there have been various attempts to increase luminescence efficiency by using 75% of energy produced by triplet state excitons produced by recombination.

The transition from a triplet state to a singlet state is a forbidden transition, is non-luminescent, and is hard to use. However, when heavy metals such as Ir, Pt, Rh, and Pd are included in luminescent materials, excitons can transit from a triplet state to a singlet state due to a property rendered by a spin-orbital coupling.

By using tris-orthometalated complex of Iridium (III), $Ir(ppy)_3$, in which three 2-phenylpyridine ligands are coordinated to Ir(III), as a light emitting layer-forming material, the external quantum efficiency may increase up to 8%, which is higher than the maximum external quantum efficiency, that is, at most 5%, of standard fluorescent materials, and this was reported in 1999 (Applied Physics Letters, Vol. 75, P.4 (1999)). However, the application of such materials to actual displays is restrictive since these materials are limited to green luminescence. Thus, it is necessary to develop phosphorescent materials, which emit light in other color ranges.

The complexes in which an aromatic based compound consisting of a carboxylic acid group as a binding site with iridium was introduced as a ligand, are used as phosphorescent materials for organic electroluminescent devices. A particular example of such a compound includes a compound in which trifluoroacetate is introduced into a 2-phenylpyridine based Ir(III) compound (U.S. Pat. Appl. No. 2002/0048689 A1).

SUMMARY OF THE INVENTION

It is an object of the present invention to provide an organometallic complex that possesses excellent luminescence properties in the range of the blue wavelengths.

It is also an object of the present invention to provide an organic electroluminescent display employing the organometallic complex.

These and other objects may be achieved by an organometallic complex represented by Formula 1 below:

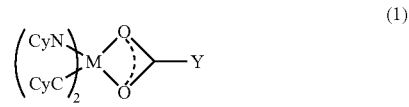

(1)

Wherein:

M is Ir, Pt, Rh or Pd;

CyN is a substituted or unsubstituted C3-C60 heterocyclic group having a nitrogen bonded to M, a substituted or unsubstituted C3-C60 aryl group having a nitrogen bonded to M or a substituted or unsubstituted C3-C60 heteroaryl group having a nitrogen bonded to M;

CyC is a substituted or unsubstituted C4-C60 carbocyclic group having a carbon bonded to M, a substituted or unsubstituted C3-C60 heterocyclic group having a carbon bonded to M, a substituted or unsubstituted C3-C60 aryl group having a carbon bonded to M or a substituted or unsubstituted C3-C60 heteroaryl group having a carbon bonded to M; or CyC and CyN can be linked together; and Y is a substituted or unsubstituted C2-C30 aryl group or a substituted or unsubstituted C2-C30 heteroaryl group.

According to another aspect of the present invention, there is provided an organic electroluminescent display comprising an organic film interposed between a pair of electrodes. The organic film comprises the organometallic complex as described above.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
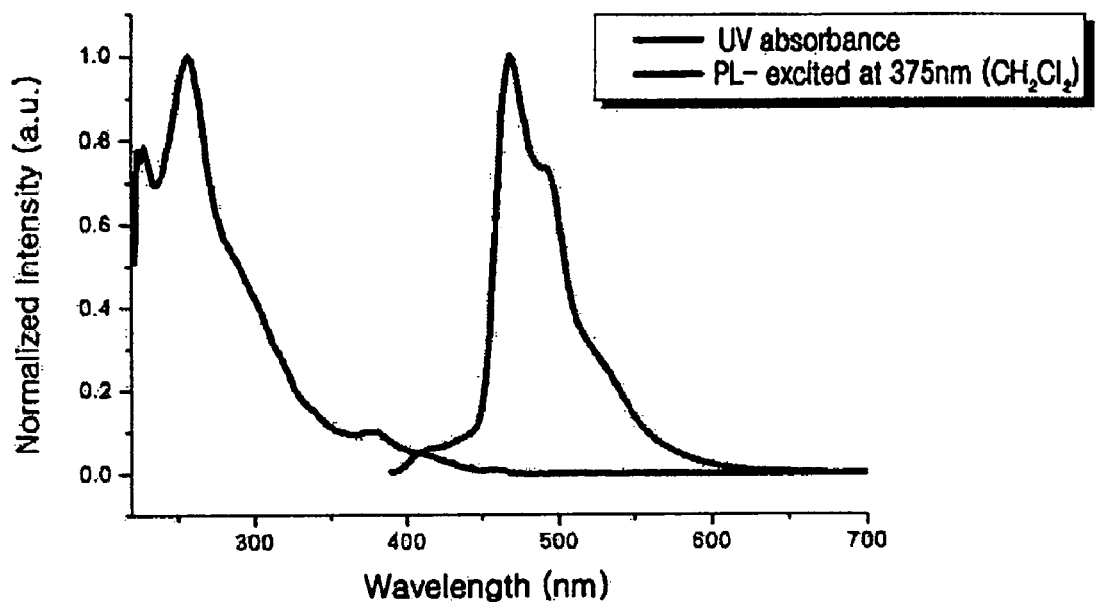
FIG. 1A illustrates a UV-VIS absorption spectrum and a photoluminescence (PL) spectrum of a compound of Formula 3 according to an embodiment of the present invention.

The present invention provides an organometallic complex having Formula 1:

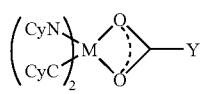

(1)

Wherein:

M is Ir, Pt, Rh or Pd;

CyN is a substituted or unsubstituted C3-C60 heterocyclic group having a nitrogen bonded to M, a substituted or unsubstituted C3-C60 aryl group having a nitrogen bonded to M or a substituted or unsubstituted C3-C60 heteroaryl group having a nitrogen bonded to M;

CyC is a substituted or unsubstituted C4-C60 carbocyclic group having a carbon bonded to M, a substituted or unsubstituted C3-C60 heterocyclic group having a carbon bonded to M, a substituted or unsubstituted C3-C60 aryl group having a carbon bonded to M or a substituted or unsubstituted C3-C60 heteroaryl group having a carbon bonded to M; or CyC and CyN can be linked together; and Y is a substituted or unsubstituted C2-C30 aryl group or a substituted or unsubstituted C2-C30 heteroaryl group.

In the organometallic complex of Formula 1, CyN and CyC are linked by a covalent bond, and CyN and CyC can each independently be substituted with a halogen atom, a nitro group, —Si($R_1$)($R_2$)($R_3$) (wherein $R_1$, $R_2$ and $R_3$ are each independently a C1-C8 alkyl group), or a C1-C20 alkyl group having at least one methylene group, and the methylene group can be substituted with —O—, —S—, —CO—, —CO—O—, —O—CO—, —CH=CH—, or —C≡C—, and can have a halogen atom. The specific examples include —$CH_2O$—$C_nH_{2n+1}$ and —$CH_2COC_nH_{2n+1}$, wherein n is an integer from 1 to 20.

The heterocyclic group and the heteroaryl group respectively represent a cyclic group and an aryl group containing a hetero atom such as N, O or S.

In the CyN of Formula 1, the substituted or unsubstituted C3-C60 heterocyclic group having a nitrogen bonded to M may be one of pyrrolidine, morpholine, thiomorpholine, thiazolidine and the like; the substituted or unsubstituted $C_3$-$C_{60}$ aryl group having a nitrogen bonded to M may be one of pyridine, 4-methoxy pyridine, quinoline, pyrrole, indole and the like; the substituted or unsubstituted C3-C60 heteroaryl group having a nitrogen bonded to M may be one of pyrazine, pyrazole, imidazole, pyrimidine, quinazoline, thiazole, oxazole, triazine, 1,2,4-triazole and the like.

In the CyC of Formula 1, the substituted or unsubstituted C4-C60 carbocyclic group having a carbon bonded to M may be one of cyclohexane, cyclopentane and the like; the substituted or unsubstituted C3-C60 heterocyclic group having a carbon bonded to M may be one of tetrahydrofuran, 1,3-dioxane, 1,3-dithiane, 1,3-dithiolane, 1,4-dioxa-8-azaspiro[4,5]decane, 1,4-dioxaspiro[4,5]decan-2-one and the like; the substituted or unsubstituted C3-C60 aryl group having a carbon bonded to M may be one of phenyl, 1,3-benzodioxole, biphenyl, naphthalene, anthracene, azulene and the like; the substituted or unsubstituted C3-C60 heteroaryl group having a carbon bonded to M may be one of thiophene, furan-2-(5H)-furanone, pyridine, coumarin, imidazole and the like. The combination of CyC and CyN linked together may be one of 2-phenylpyridine, benzothiazole, benzoxazole, 1-phenylpyrazole, 1-naphthylpyrazole, 5-(4-methoxyphenyl)pyrazole, 2,5-bisphenyl-1,3,4-oxadiazole, 2,3-benzofuran-2-(4-biphenyl)-6-phenyl benzoxazole and the like.

Y can include substituents such as C1-C30, preferably C1-C20, more preferably C1-C10 alkyl group (for example, methyl, ethyl, isopropyl, t-butyl, n-octyl, n-decyl, n-hexadecyl, cyclopropyl, cyclopentyl, cyclohexyl and the like); a C1-C30 halogenated alkyl (for example, trifluoromethyl); a C2-C30, preferably C2-C20, more preferably C2-C10 alkenyl group (for example, vinyl, allyl, 2-butenyl, 3-pentyl and the like); a C2-C30, preferably C2-C20, more preferably C2-C10 alkynyl group (for example, propargyl, 3-pentynyl and the like); a C6-C30, preferably C6-C20, more preferably C6-C12 aryl group (for example, phenyl, p-methylphenyl, naphthyl, anthranyl and the like); an amino group; a C1-C30, preferably C1-C20, more preferably C1-C10 alkylamino group (for example, methylamino, dimethylamino, diethylamino, dibenzylamino, diphenylamino, ditolylamino and the like); a C1-C30, preferably C1-C20, more preferably C1-C10 alkoxy group (for example, methoxy, ethoxy, butoxy, 2-ethylhexyloxy and the like); a C6-C30, preferably C6-C20, more preferably C6-C10 aryloxy group (for example, phenyloxy, 1-naphthyloxy, 2-naphthyloxy and the like); a C1-C30, preferably C1-C20, more preferably C2-C10 heteroaryloxy group (for example, pyridyloxy, pyrazolyloxy, pyrimidyloxy, quinolyloxy and the like); a C1-C30, preferably C1-C20, more preferably C1-C10 acyl group (for example, acetyl, benzoyl, formyl, pivaloyl and the like); a C2-C30, preferably C2-C20, more preferably C2-C10 alkoxycarbonyl group (for example, methoxycarbonyl, ethoxycarbonyl and the like); a C7-C30, preferably C7-C20, more preferably C7-C10 aryloxycarbonyl group (for example, phenyloxycarbonyl and the like); a C2-C30, preferably C2-C20, more preferably C2-C10 acyloxy group (for example, acetoxy, benzoyloxy and the like); a C2-C30, preferably C2-C20, more preferably C2-C10 acylamino group (for example, acetylamino, benzoylamino and the like); a C2-C30, preferably C2-C20, more preferably C2-C10 alkoxycarbonylamino group (for example, methoxycarbonylamino and the like); a C7-C30, preferably C7-C20, more preferably C7-C10aryloxycarbonylamino group (for example, phenyloxycarbonylamino and the like); a C1-C30, preferably C1-C20, more preferably C1-C12 sulfonylamino group (for example, methanesulfonylamino, benzenesulfonylamino and the like); a sulfamoyl group; a C1-C30, preferably C1-C20, more preferably C1-C12 alkylsulfamoyl group (for example, methylsulfamoyl, dimethyl sulfamoyl, phenylsulfamoyl and the like); a carbamoyl group; a C2-C30, preferably C2-C20, more preferably C2-C12 alkylcarbamoyl group (for example, methylcarbamoyl, diethylcarbamoyl, phenylcarbamoyl and the like); a C1-C30, preferably C1-C20, more preferably C1-C12 alkylthio group (for example, methylthio, ethylthio and the like); a C6-C30, preferably C6-C20, more preferably C6-C12 arylthio group (for example, phenylthio and the like); a C1-C30, preferably C1-C20, more preferably C1-C12 heteroarylthio group (for example, pyridylthio, 2-benzimidazolylthio, 2-benzoxazolylthio, 2-benzothiazolylthio and the like); a C1-C30, preferably C1-C20, more preferably C1-C12 alkylsulfonyl group (for example, mesyl, tosyl); a C1-C30, preferably C1-C20, more preferably C1-C12 alkylsulfinyl group (for example, methanesulfonyl and benzenesulfonyl); ureido group; C2-C30, preferably C2-C20, more preferably C2-C12 alkylureido group (for example, methylureido, phenylureido); a C1-C30, preferably C1-C20, more preferably C1-C12 phosphoric acid amido group (for example, phosphoric acid amido, diethylphosphoric acid amido, phenyl phosphoric acid amido); a hydroxy group; a mercapto group; a halogen atom (for example, fluorine, chlorine, bromine, iodine); a halide (for example, trifluoromethyl); a cyano group; a sulfo group; a carboxylic group, a nitro group, a hydroxamic acid group, a sulfino group; a hydrazino group; an imino group; a C1-C30, preferably C1-C12 heterocyclic group (e.g., aliphatic heterocyclic group, heteroaryl group) having one or more heteroatom such as O, N or S (for example, imidazolyl, pyridyl, quinolyl, furyl, thienyl, piperidyl, morpholino, benzoxazolyl, benzimidazolyl, benzothiazolyl and the like); a C3-C40, preferably C3-C30, more preferably C3-C24 alkylsilyl group (for example, trimethylsilyl, triphenylsilyl); and a C2-C30, preferably C2-C20 alkylphosphino group (for example, dimethylphosphino, diphenylphosphino).

The compound of Formula 1 is preferably the compound of formula 2:

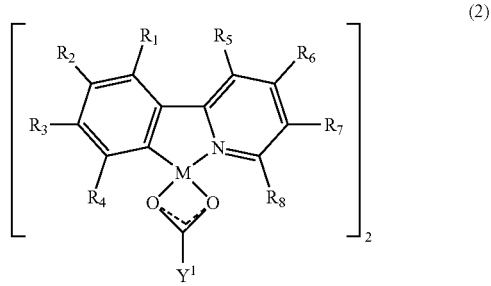

(2)

wherein M is Ir, Pt, Rh or Pd;

$R_1$, $R_2$, $R_3$, $R_4$, $R_5$, $R_6$, $R_7$ and $R_8$ are independently a hydrogen atom, C1-C30 alkyl group, C2-C30 alkenyl group, a halogen atom, a halide, a amino group, a hydroxy group, a mercapto group, a cyano group, a sulfonyl group or a sulfinyl group, and at least two adjacent R's(R1 to R8) can be interconnected to form a ring; and Y' is a substituted or unsubstituted C2-C30 aryl group or a substituted or unsubstituted C2-C30 heteroaryl group.

For Formula 2, M is preferably Ir (iridium).

The compound of Formula 1 according to an embodiment of the present invention produces light at wavelengths in the ranges of 390 to 650 nm.

The organometallic complex of Formula 2 is preferably an iridium complex represented by one of the following Formulas 3 through 6:

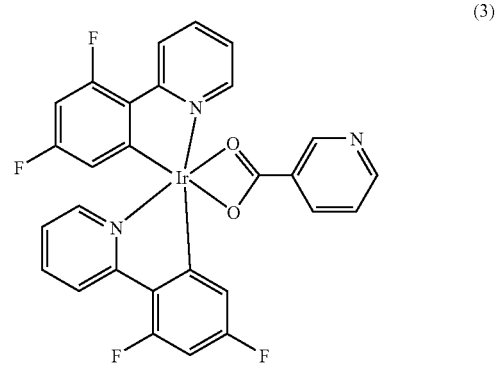

(3)

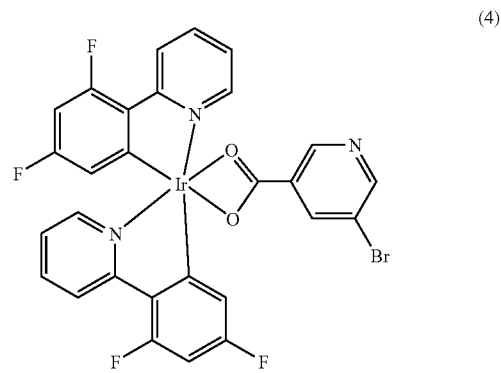

(4)

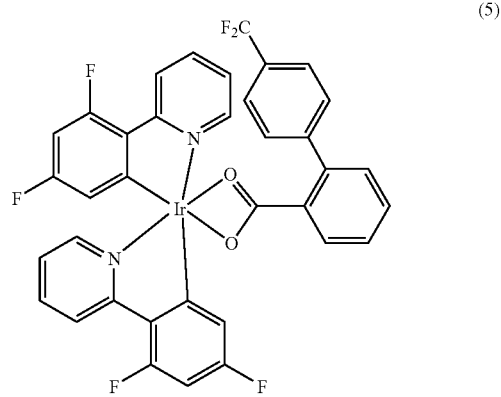

(5)

-continued

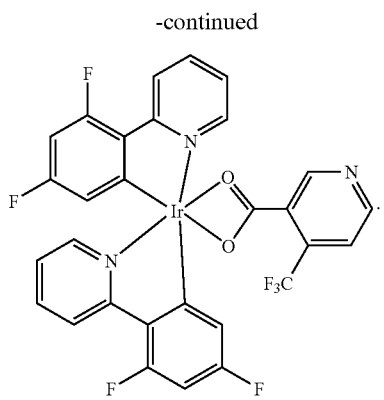
(6)

The organic electroluminescent device of the present embodiment is prepared by forming an organic film, particularly a light emitting layer employing the organometallic complex of Formula 1. The organometallic complex of Formula 1 is very useful as a phosphorescence dopant material that is a light emitting layer-forming material, and possesses excellent luminescence properties in the range of the blue wavelengths.

The concentration of the organometallic complex of Formula 1 in the light-emitting layer is 1 to 30% by weight based on the total weight of materials for forming the light-emitting layer. The inclusion of the organometallic complex in the light emitting layer can be carried out by one of vacuum vapor deposition, sputtering, printing, coating, ink jetting, a technique using electronic beam and the like.

When the organometallic complex of Formula 1 is used as a phosphorescence dopant, any conventional material that can be used for forming a light-emitting layer of organic electroluminescent devices can be used as a host. The conventional materials may be PVK (polyvinylcarbazole), CBP (4,4'-N,N'-dicarbazole-biphenyl), 4,4'-bis[9-(3,6-biphenylcarbazolyl)]-1-1,1'-biphenyl, 9,10-bis[(2',7'-t-butyl)-9,9'-spiro bifluorenylanthracene, or tetrafluorene.

The thickness of the organic film is preferably 50 to 100 nm. The organic film used herein refers to films of organic compounds, such as an electron transporting layer and a hole transporting layer as well as a light emitting layer, which are formed between a pair of electrodes in organic electroluminescent display.

Conventionally, the organic electroluminescent display can have various structures, for example anode/light emitting layer/cathode, anode/buffer layer/light emitting layer/cathode, anode/hole transporting layer/light emitting layer/cathode, anode/buffer layer/hole transporting layer/light emitting layer/cathode, anode/buffer layer/hole transporting layer/light emitting layer/transporting layer/cathode, anode/buffer layer/hole transporting layer/light emitting layer/hole blocking layer/anode and the like, but the present invention is not limited to these examples.

The buffer layer is composed of a material commonly used for a buffer layer, and is preferably composed of copper phthalocyanine, polythiophene, polyaniline, polyacetylene, polypyrrole, polyphenylene vinylene or their derivatives.

The hole transporting layer is composed of a material commonly used for a hole transporting layer, and is preferably composed of polytriphenylamine can be used.

The electron transporting layer is composed of a material commonly used for an electron transporting layer, and is preferably composed of polyoxadiazole.

The hole blocking layer can be composed of a material that can be commonly used for a hole blocking layer, and preferably, BCP (2,9-dimethyl-4,7-diphenyl-phenanthroline) can be used.

The organic electroluminescent display of the present embodiment invention can be prepared by a conventional method of manufacturing an organic electroluminescent display employing conventional luminescent materials, and thus does not need special apparatuses or processes.

The present invention will be described in greater detail with reference to the following examples. The following examples are for illustrative purposes and are not intended to limit the scope of the invention.

EXAMPLES

In the following examples, an iridium complex was prepared using Schlenk technique or Glove box technique under a nitrogen atmosphere excluding moisture or oxygen. The synthetic pathway is illustrated sequentially in the following scheme:

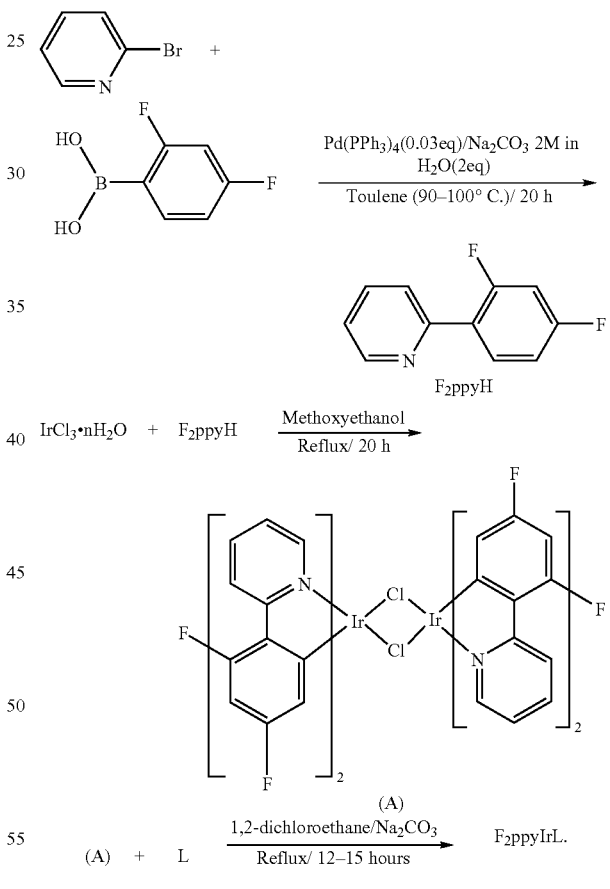

When L is

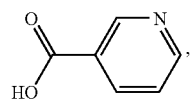

the product is the compound of Formula 3 (Nico).

When L is

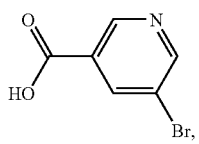

the product is the compound of Formula 4 (Nico(Br)).

When L is

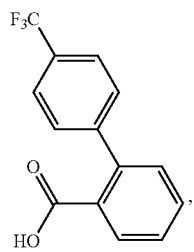

the product is the compound of Formula 5 (CF$_3$PhBen).

When L is

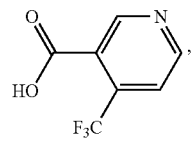

the product is the compound of Formula 6 (CF$_3$Nico).

(1) Preparation of the Compound (F$_2$ppyH)

19.85 g (1.25×10$^4$ mmol) of 2-bromopyridine, 25.00 g(1.58×10$^4$ mmol) of 2,4-difluorophenyl boronic acid, 100 ml of toluene, 48 ml of ethanol and a solution of 2 M sodium carbonate in water (95 ml) were added in a 500 ml flask, and the mixture was agitated under a nitrogen atmosphere at room temperature. Then, 4.53 g (3.92 mmol) of tetrakis (triphenylphosphin) palladium(0) was added to the resulting reaction mixture, and the mixture was refluxed under the nitrogen atmosphere in a dark room for 15 hours.

After the temperature of the reaction mixture was returned to room temperature on completion of the reaction, an organic layer was extracted using ethyl acetate and water, and collected and treated several times. Then, after removing the solvent, the resulting residue was purified by silica gel column chromatography (toluene:hexane=10:1 volumetric ratio), producing a brown liquid.

$^1$H-NMR(CD$_2$Cl$_2$, ppm):8.69[d, 1H], 8.03[m, 1H], 7.70 [m, 2H], 7.27[m, 1H], 7.00[m, 2H].

(2) Preparation of the Ir Dimer

Ir dimer was prepared by the method described in J. Am. Chem. Soc. Vol. 106, P. 6647 (1984), which is incorporated by reference herein.

(3) Preparation of the Iridium Complex of Formula 3.

0.536 g (0.5 mmol) of the dimer intermediate (A) synthesized in the example (2) above, 0.148 g (1.2 mmol) of nicotinic acid and 0.105 g (1 mmol) of Na$_2$CO$_3$ were added to a flask and air in the flask was replaced with nitrogen. Then, 60 ml of dichloroethane was added to the reaction mixture, and was agitated under a nitrogen atmosphere at room temperature. The resulting mixture was recrystallized with methylene chloride and hexane, producing a yellow powder.

$^1$H-NMR(CD$_2$Cl$_2$, ppm):9.35[d, 1H], 9.0–8.0[m, 6H], 7.87[m, 2H], 7.48[m, 2 1H], 7.40[m, 2H], 5.72[m, 1H], 5.53[m, 1H].

(4) Preparation of the Iridium Complex of Formula 4.

0.536 g (0.5 mmol) of the dimer intermediate(A) synthesized in (2) above, 0.242 g (1.2 mmol) of 5-bromo nicotinic acid and 0.105 g (1 mmol) of Na$_2$CO$_3$ were added to a flask, and the air in the flask was replaced with nitrogen. Then, 60 ml of dichloroethane was added to the mixture, and the mixture was agitated under a nitrogen atmosphere at room temperature. The resulting mixture was recrystallized with methylene chloride and hexane, producing a yellow powder.

$^1$H-NMR(CD$_2$Cl$_2$, ppm):10.79[d, 1H], 9.24[d, 1H], 9.0–7.6[m, 7H], 7.42[m, 1H], 6.98[m, 1H], 6.44[m, 2H], 5.78[m, 1H], 5.61[m, 1H].

(5) Preparation of the Iridium Complex of Formula 5.

0.536 g (0.5 mmol) of the dimer intermediate(A) synthesized in (2) above, 0.319 g (1.2 mmol) of 4'-(trifluoromethyl)-2-biphenylcarboxylic acid and 0.105 g (1 mmol) of Na$_2$CO$_3$, were added to a flask, and the air in the flask was replaced with nitrogen. Then, 60 ml of dichloroethane was added to the mixture, and the mixture was agitated under a nitrogen atmosphere at room temperature. The resulting mixture was recrystallized with methylene chloride and hexane, producing a yellow powder.

$^1$H-NMR(CD$_2$Cl$_2$, ppm):8.55[d, 2H], 8.22[d, 2H], 7.83[t, 2H], 7.77[d,1H], 7.20–7.40[m, 9H], 6.3[m, 2H], 5.38[m, 2H].

(6) Preparation of the Iridium Complex of Formula 6.

0.536 g (0.5 mmol) of the dimer intermediate(A) synthesized in (2) above, 0.229 g (1.2 mmol) of 4-(trifluoromethyl) nicotinic acid and 0.105 g (1 mmol) of Na$_2$CO$_3$, were added to a flask, and the air in the flask was replaced with nitrogen. Then, 60 ml of dichloroethane was added to the mixture, and the mixture was agitated under a nitrogen atmosphere at room temperature. The resulting mixture was recrystallized with methylene chloride and hexane, producing a yellow powder.

$^1$H-NMR(CD$_2$Cl$_2$, ppm):9.11[d, 1H], 9.0–7.7[m, 7H], 7.58[d, 1H]7.32[t,1H], 7.05[t, 1H], 6.35[m, 2H], 5.55[m, 1H], 5.45[m, 1H].

The optical properties of the compounds of Formulae 3 to 6 were measured by measuring their absorption spectrum (UV-VIS spectrum), the photoluminescence spectrum (PL spectrum) and the time resolved photoluminescence. The measurements were carried out at room temperature, and the time resolved transient PL was determined using an ISSPC spectrofluorometer and a laser (N$_2$, pulse width:800 ps) at 337 mn.

PL test samples were prepared as follows:

10$^{-4}$ M solutions were prepared in methylene chloride, and films were prepared by mixing test samples (5% by weight) and polymethylmethacrylate (PMMA) (95% by weight), producing 1% by weight solution in chlorobenzene and then spin-coating the solutions.

The PL values of the compounds are shown in Table 1 below, and the PL spectra are shown in FIGS. 1A to 4.

TABLE 1

| | PL λmax(nm): Solution[a] | PL λmax(nm): Film(PMMA)[b] |
|---|---|---|
| Formula 3 [F$_2$ppyIrNico] | 468 | 470 |
| Formula 4 [F$_2$ppyIrNico(Br)] | 470 | 464 |
| Formula 5 [F$_2$ppyIrCF$_3$PhBez] | 480 | 470 |
| Formula 6 [F$_2$ppyIrCF$_3$Nico] | 468 | 470 |

[a]: $10^{-4}$ M solution in methylene chloride
[b]: doped with 5% by weight in polymethylmethacrylate As shown in table 1, all the organometallic complexes prepared according to embodiments of the present invention exhibited approximately consistent PL maximum wavelengths in both the solution and film states.

Figure 1B:
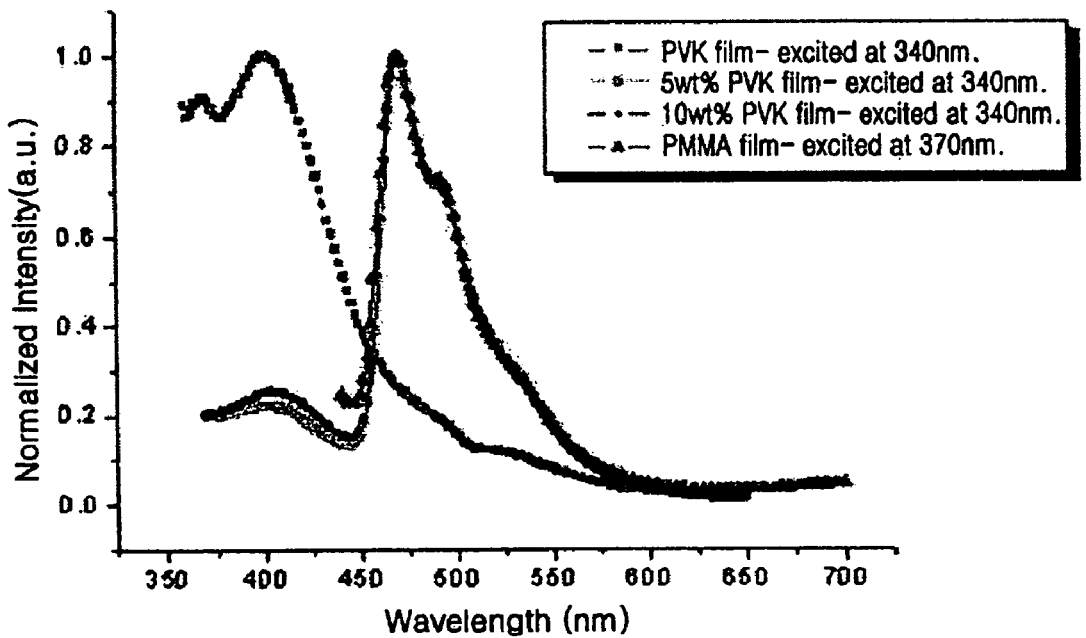
FIG. 1B illustrates a PL spectrum of a compound of Formula 3 in the form of film according to an embodiment of the present invention.
Figure 2:
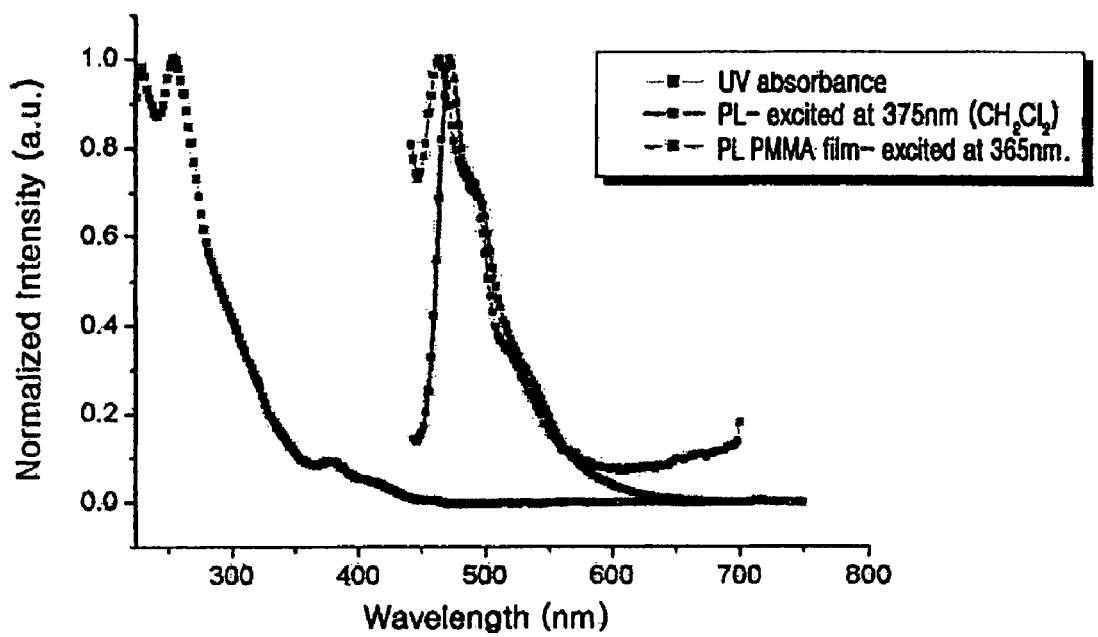
FIG. 2 illustrates a UV-VIS absorption spectrum and a PL spectrum of a compound of Formula 4 according to an embodiment of the present invention.
Figure 3:
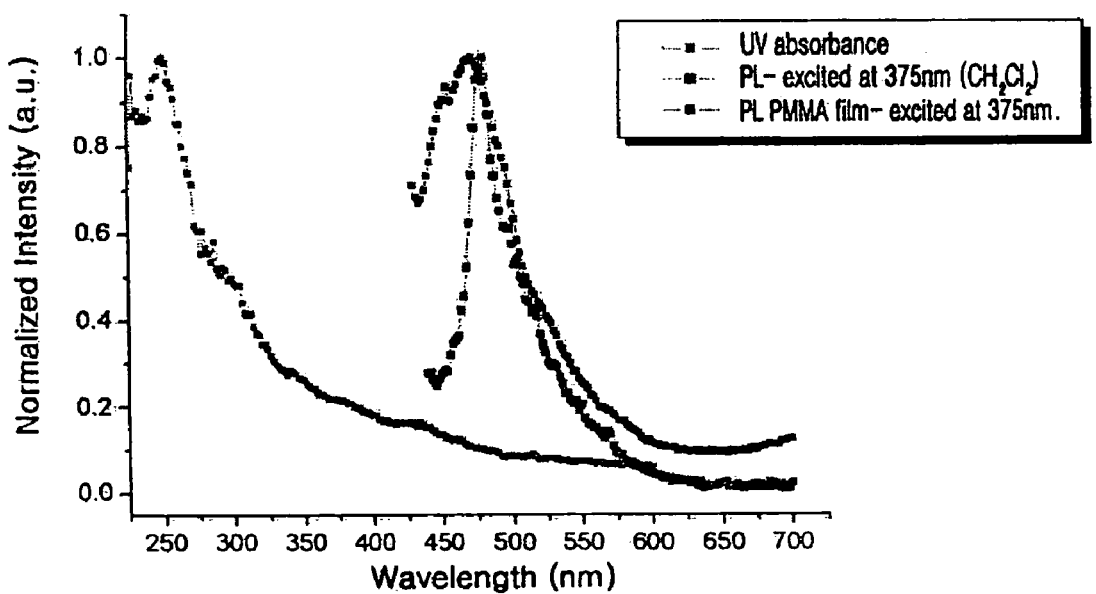
FIG. 3 illustrates a UV-VIS absorption spectrum and a PL spectrum of a compound of Formula 5 according to an embodiment of the present invention.
Figure 4:
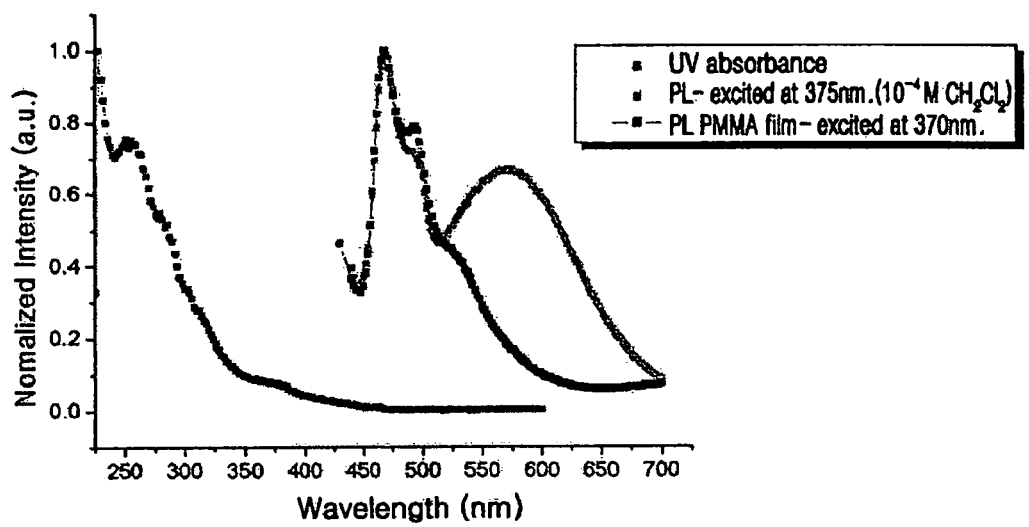
FIG. 4 illustrates a UV-VIS absorption spectrum and a PL spectrum of a compound of Formula 6 according to an embodiment of the present invention.

Also, to assess the applicability of the organometallic complexes according to the embodiments of the present invention to a light emitting layer, each 5% by weight and 10% by weight of F$_2$ppyIrNico was added to PVK as a host material, and then the resulting mixture was dissolved in chlorobenzene to produce 1% by weight solution of chlorobenzene, and then spincoated (see FIG. 1B).

PL spectra of the doped PVK film was recorded. A result of the measurements show that the PL peak of PVK was not observed, and only PL peak of F$_2$ppyIrNico compound was observed. From the results, it can be found that the energy transfer from PVK to F$_2$ppyIrNico occurred well, and thus almost only luminescence of F$_2$ppyIrNico occurred.

Figure 5:
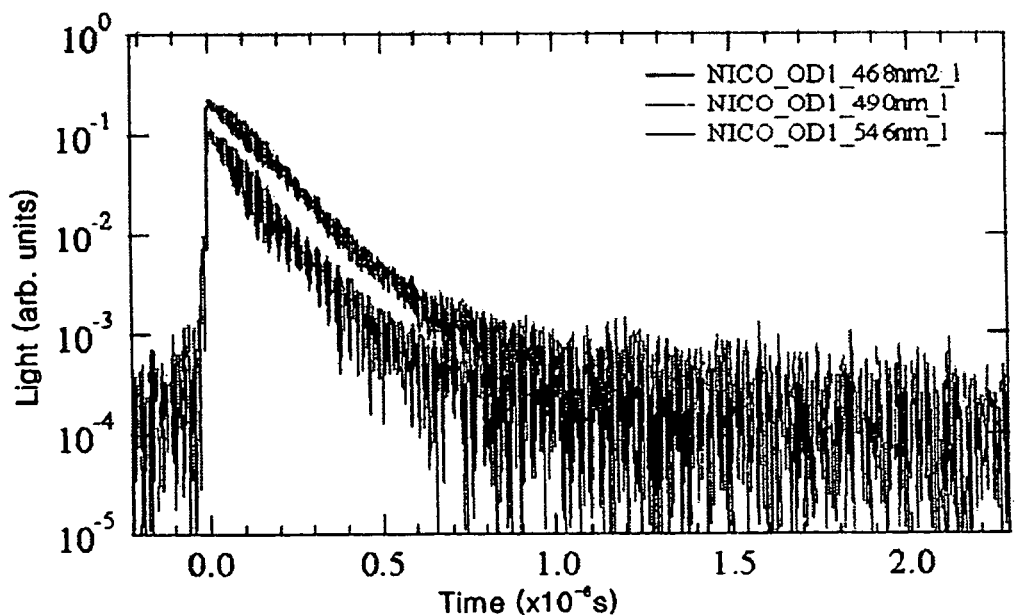
FIG. 5 illustrates the radiative decay time of a compound of Formula 4 in a $CH_2Cl_2$ solution.

Luminescence decay times of the synthesized organometallic complexes were determined using $10^{-4}$ M solutions in methylene chloride. The results are shown in Table 2 and FIG. 5.

TABLE 2

| | PL λmax(nm) | Decay time (μsec) |
|---|---|---|
| Formula 3 [F$_2$ppyIrNico] | 468 | 0.135 |
| Formula 4 [F$_2$ppyIrNico(Br)] | 470 | 0.374 |
| Formula 5 [F$_2$ppyIrCF3PhBez] | 480 | 0.250 |
| Formula 6 [F$_2$ppyIrCF3Nico] | 468 | 0.420 |

It was found from the above results of the luminescence decay time that the PL of the compound was phosphorescence since the luminescence decay times are observed in lisec range.

As illustrated above, the present invention relates to an organometallic complex comprising carboxylic acid as an ancillary ligand and an organic electroluminescent display employing the same. The organometallic complex is useful as a phosphorescence dopant material of an organic electroluminescent device due to its high luminosity in the range of the blue wavelengths.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organometallic complex represented by Formula 1:

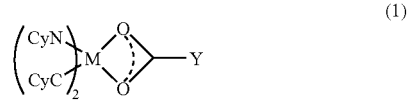

(1)

wherein:

M is selected from the group consisting of Ir, Pt, Rh and Pd;

CyN is selected from the group consisting of a substituted or unsubstituted C3-C60 heterocyclic group having a nitrogen bonded to M, a substituted or unsubstituted C3-C60 heteroaryl group having a nitrogen bonded to M;

CyC is selected from the group consisting of a substituted or unsubstituted C4-C60 carbocyclic group having a carbon bonded to M, a substituted or unsubstituted C3-C60 heterocyclic group having a carbon bonded to M, a substituted or unsubstituted C3-C60 aryl group having a carbon bonded to M, and a substituted or unsubstituted C3-C60 heteroaryl group having a carbon bonded to M; and Y is a substituted C2-C30 aryl group or a substituted C2-C30 heteroaryl group, and Y is substituted with at least one group selected from the group consisting of a C1-C30 alkyl group, a halogenated C1-C30 alkyl group, a C2-C30 alkenyl group, a C2-C30 alkynyl group, a C6-C30 aryl group, an amino group, a C1-C30 alkylamino group, a C1-C30 alkoxy group, a C6-C30 aryloxy group, a C1-C30 heteroaryloxy group, a C1-C30 acyl group, a C2-C30 alkoxycarbonyl group, a C7-C30 aryloxycarbonyl group, a C2-C30 acyloxy group, a C2-C30 acylamino group, a C2-C30 alkoxycarbonylamino group, a C7-C30 aryloxycarbonylamino group, a C1-C30 sulfonylamino group, a sulfamoyl group, a C1-C30 alkylsulfamoyl group, a carbamoyl group, a C2-C30 alkylcarbamoyl group, a C1-C30 alkylthio group, a C6-C30 arylthio group, a C1-C30 heteroarylthio group, a C1-C30 alkylsulfonyl group, a C1-C30 alkylsulfinyl group, a ureido group, a C1-C30 alkylureido group, a C1-C30 phosphoric acid amino group, a hydroxy group, a mercapto group, a halogen atom, a halide, a cyano group, a sulfo group, a carboxyl group, a nitro group, a hydroxamic acid group, a sulfino group, a hydrazino group, an imino group, a C1-C30 heterocyclic group, a C3-C40 alkylsilyl group, a C2-C30 alkylphosphino group, triphenylsilyl and diphenylphosphino.

2. The organometallic complex of claim 1, wherein CyN and CyC are linked by a covalent bond, and CyN and CyC are each substituted with one selected from the group consisting of a halogen atom, a nitro group, —Si(R$_1$)(R$_2$)(R$_3$) in which R$_1$, R$_2$ and R$_3$ are each independently selected from the group consisting of a C1-C8 alkyl group, a C1-C20 alkyl group having at least one methylene group, a C1-C20 alkyl group having at least one methylene group substituted with one selected from the group consisting of —O—, —S—, —CO—, —CO—O—, —O—CO—, —CH=CH— and —C≡C—, and a C1-C20 alkyl group having at least one methylene group having a halogen atom.

3. The organometallic complex of claim 1, wherein CyN is selected from the group consisting of pyrrolidine, morpholine, thiomorpholine, thiazolidine, pyridine, 4-methoxy pyridine, quinoline, pyrrole, indole, pyrazine, pyrazole, imidazole, pyrimidine, quinazoline, thiazole, oxazole, triazine, and 1,2,4-triazole.

4. The organometallic complex of claim 1, wherein CyC is selected from the group consisting of cyclohexane, cyclopentane, tetrahydrofuran, 1,3-dioxane, 1,3-dithiane, 1,3-dithiolane, 1,4-dioxa-8-azaspiro [4,5]decane, 1,4-dioxaspiro [4,5]decan-2-one, phenyl, 1,3-benzodioxole, biphenyl, naphthalene, anthracene, azulene, thiophene, furan-2-(5H)-furanone, pyridine, coumarin, and imidazole.

5. The organometallic complex of claim 1, wherein said CyC and said CyN are linked together to form a combined group selected from the group consisting of 2-phenylpyridine, benzothiazole, benzoxazole, 1-phenylpyrazole, 1-naphthylpyrazole, 5-(4-methoxyphenyl)pyrazole, 2,5-bisphenyl-1,3,4-oxadiazole, and 2,3-benzofuran-2-(4-biphenyl)-6-phenyl benzoxazole.

6. The organometallic complex of claim 1, wherein Y is substituted with at least one group selected from the group consisting of methyl, ethyl, isopropyl, t-butyl, n-octyl, n-decyl, n-hexadecyl, cyclopropyl, cyclopentyl, cyclohexyl, trifluoromethyl, vinyl, allyl, 2-butenyl, 3-pentyl, propargyl, 3-pentynyl, phenyl, p-methylphenyl, naphthyl, anthranyl, methylamino, dimethylamino, diethylamino, dibenzylamino, diphenylamino, ditolylamino, methoxy, ethoxy, butoxy, 2-ethylhexyloxy, phenyloxy, 1-naphthyloxy, 2-naphthyloxy, pyridyloxy, pyrazolyloxy, pyrimidyloxy, quinolyloxy, acetyl, benzoyl, formyl, pivaloyl, methoxycarbonyl, ethoxycarbonyl, phenyloxycarbonyl, acetoxy, benzoyloxy, acetylamino, benzoylamino, methoxycarbonylamino, phenyloxycarbonylamino, methanesulfonylamino, benzenesulfonylamino, methylsulfamoyl, dimethyl sulfamoyl, phenylsulfamoyl, methylcarbamoyl, diethylcarbamoyl, phenylcarbamoyl, methylthio, ethylthio, phenylthio, pyridylthio, 2-benzimidazolylthio, 2-benzoxazoylthio, 2-benzothiazolylthio, mesyl, tosyl, methanesulfonyl, benzenesulfonyl, methylureido, phenylureido, phosphoric acid amido, diethylphosphoric acid amido, phenyl phosphoric acid amido, fluorine, chlorine, bromine, iodine, trifluoromethyl, imidazolyl, pyridyl, quinolyl, furyl, thienyl, piperidyl, morpholino, benzoxazolyl, benzimidazolyl, benzothiazolyl, trimethylsilyl, triphenylsilyl, dimethylphosphino, and diphenylphosphino.

7. The organometallic complex of claim 1, wherein said organometallic complex is represented by Formula 2:

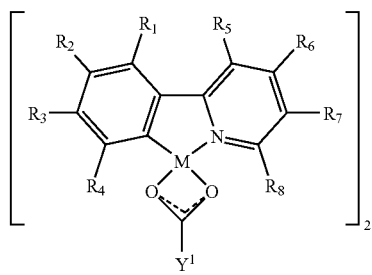

(2)

wherein M is selected from the group consisting of Ir, Pt, Rh and Pd;

$R_1$, $R_2$, $R_3$, $R_4$, $R_5$, $R_6$, $R_7$ and $R_8$ are independently selected from the group consisting of a hydrogen atom, a C1-C30 alkyl group, a C2-C30 alkenyl group, a halogen atom, a halide, an amino group, a hydroxy group, a mercapto group, a cyano group, a sulfonyl group and a sulfinyl group, and at least two adjacent groups of $R_1$ to $R_4$ and $R_5$ to $R_8$ can be interconnected to form a ring; and Y' is a substituted C2-C30 aryl group or a substituted C2-C30 heteroaryl group, and Y' is substituted with at least one group selected from the group consisting of a C1-C30 alkyl group, a halogenated C1-C30 alkyl group, a C2-C30 alkenyl group, a C2-C30 alkynyl group, a C6-C30 aryl group, an amino group, a C1-C30 alkylamino group, a C1-C30 alkoxy group, a C6-C30 aryloxy group, a C1-C30 heteroaryloxy group, a C1-C30 acyl group, a C2-C30 alkoxycarbonyl group, a C7-C30 aryloxycarbonyl group, a C2-C30 acyloxy group, a C2-C30 acylamino group, a C2-C30 alkoxycarbonylamino group, a C7-C30 aryloxycarbonylamino group, a C1-C30 sulfonylamino group, a sulfamoyl group, a C1-C30 alkylsulfamoyl group, a carbamoyl group, a C2-C30 alkylcarbamoyl group, a C1-C30 alkylthio group, a C6-C30 arylthio group, a C1-C30 heteroarylthio group, a C1-C30 alkylsulfonyl group, a C1-C30 alkylsulfinyl group, a ureido group, a C1-C30 alkylureido group, a C1-C30 phosphoric acid amino group, a hydroxy group, a mercapto group, a halogen atom, a halide, a cyano group, a sulfo group, a carboxyl group, a nitro group, a hydroxamic acid group, a sulfino group, a hydrazino group, an imino group, a C1-C30 heterocyclic group, a C3-C40 alkylsilyl group, and a C2-C30 alkylphosphino group.

8. The organometallic complex of claim 7, wherein M is iridium.

9. An organic electroluminescent display comprising an organic film interposed between a pair of electrodes, wherein the organic film comprises the organometallic complex of claim 7.

10. An organic electroluminescent display comprising an organic film interposed between a pair of electrodes, wherein the organic film comprises the organometallic complex of claim 1.

11. An organometallic complex represented by a formula selected from the group consisting of Formulae 4 through 6:

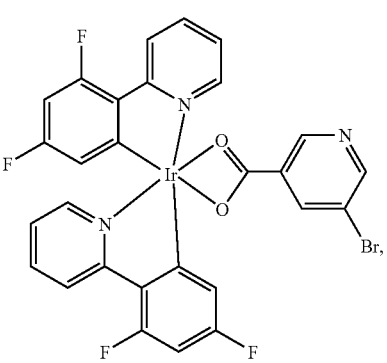

(4)

-continued

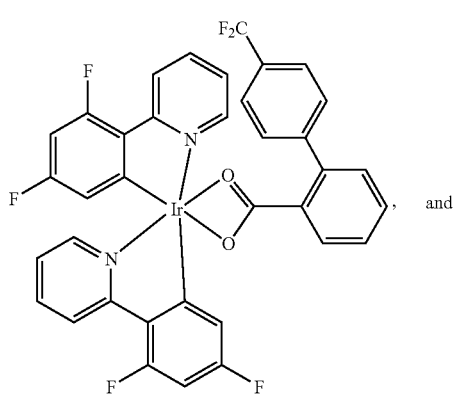

(5)

, and

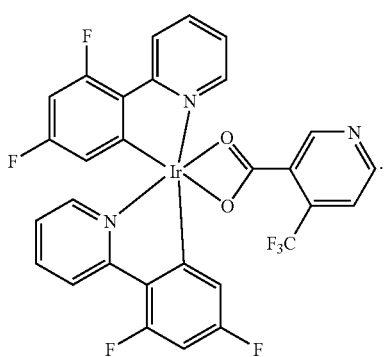

(6)

12. An organic electroluminescent display comprising an organic film interposed between a pair of electrodes, wherein the organic film comprises the organometallic complex of claim 11.

13. An organic electroluminescent display, comprising:
a pair of electrodes; and
an organic film interposed between the pair of electrodes, said organic film comprising an organometallic complex having a photoluminescence maximum wavelength in a blue region and represented by Formula 1:

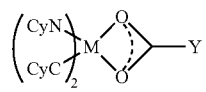

(1)

wherein M is selected from the group consisting of Ir, Pt, Rh and Pd;
CyN is selected from the group consisting of a substituted or unsubstituted C3-C60 heterocyclic group having a nitrogen bonded to M, and a substituted or unsubstituted C3-C60 heteroaryl group having a nitrogen bonded to M;
CyC is selected from the group consisting of a substituted or unsubstituted C4-C60 carbocyclic group having a carbon bonded to M, a substituted or unsubstituted C3-C60 heterocyclic group having a carbon bonded to M, a substituted or unsubstituted C3-C60 aryl group having a carbon bonded to M, and a substituted or unsubstituted C3-C60 heteroaryl group having a carbon bonded to M; and Y is a substituted C2-C30 aryl group or a substituted C2-C30 heteroaryl group, and Y is substituted with at least one group selected from the group consisting of a C1-C30 alkyl group, a halogenated C1-C30 alkyl group, a C2-C30 alkenyl group, a C2-C30 alkynyl group, a C6-C30 aryl group, an amino group, a C1-C30 alkylamino group, a C1-C30 alkoxy group, a C6-C30 aryloxy group, a C1-C30 heteroaryloxy group, a C1-C30 acyl group, a C2-C30 alkoxycarbonyl group, a C7-C30 aryloxycarbonyl group, a C2-C30 acyloxy group, a C2-C30 acylamino group, a C2-C30 alkoxycarbonylamino group, a C7-C30 aryloxycarbonylamino group, a C1-C30 sulfonylamino group, a sulfamoyl group, a C1-C30 alkylsulfamoyl group, a carbamoyl group, a C2-C30 alkylcarbamoyl group, a C1-C30 alkylthio group, a C6-C30 arylthio group, a C1-C30 heteroarylthio group, a C1-C30 alkylsulfonyl group, a C1-C30 alkylsulfinyl group, a ureido group, a C1-C30 alkylureido group, a C1-C30 phosphoric acid amino group, a hydroxy group, a mercapto group, a halogen atom, a halide, a cyano group, a sulfo group, a carboxyl group, a nitro group, a hydroxamic acid group, a sulfino group, a hydrazino group, an imino group, a C1-C30 heterocyclic group, a C3-C40 alkylsilyl group, and a C2-C30 alkylphosphino group.

14. The organic electroluminescent display of claim 13, wherein the organic film is a light emitting layer including luminescent materials.

15. The organic electroluminescent display of claim 14, wherein the concentration of the organometallic complex is 1 to 30% by weight based on total weight of the luminescent materials in the light emitting layer.

16. The organic electroluminescent display of claim 13, wherein said organometallic complex is represented by Formula 2:

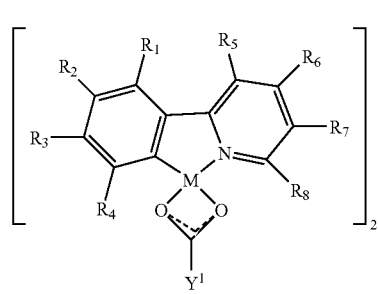

(2)

wherein M is selected from the group consisting of Ir, Pt, Rh and Pd;
$R_1$, $R_2$, $R_3$, $R_4$, $R_5$, $R_6$, $R_7$ and $R_8$ are independently selected from the group consisting of a hydrogen atom, a C1-C30 alkyl group, a C2-C30 alkenyl group, a halogen atom, a halide, an amino group, a hydroxy group, a mercapto group, a cyano group, a sulfonyl group and a sulfinyl group, and at least two adjacent groups of $R_1$ to $R_4$ and $R_5$ to $R_8$ can be interconnected to form a ring; and
Y' has the same definition as Y in claim 13.

17. An organometallic complex represented by Formula 1:

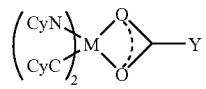

wherein:
M is selected from the group consisting of Ir, Pt, Rh and Pd;
CyN is selected from the group consisting of a substituted or unsubstituted C3-C60 heterocyclic group having a nitrogen bonded to M, and a substituted or unsubstituted C3-C60 heteroaryl group having a nitrogen bonded to M;
CyC is selected from the group consisting of a substituted or unsubstituted C4-C60 carbocyclic group having a carbon bonded to M, a substituted or unsubstituted C3-C60 heterocyclic group having a carbon bonded to M, a substituted or unsubstituted C3-C60 aryl group having a carbon bonded to M, and a substituted or unsubstituted C3-C60 heteroaryl group having a carbon bonded to M; and
Y is a substituted or unsubstituted C2-C30 aryl group or a substituted or unsubstituted C2-C30 heteroaryl group, with the proviso that Y is not pyridine, and the substituted C2-C30 aryl group or a substituted C2-C30 heteroaryl group is substituted with at least one group selected from the group consisting of a C1-C30 alkyl group, a halogenated C1-C30 alkyl group, a C2-C30 alkenyl group, a C2-C30 alkynyl group, a C6-C30 aryl group, an amino group, a C1-C30 alkylamino group, a C1-C30 alkoxy group, a C6-C30 aryloxy group, a C1-C30 heteroaryloxy group, a C1-C30 acyl group, a C2-C30 alkoxycarbonyl group, a C7-C30 aryloxycarbonyl group, a C2-C30 acyloxy group, a C2-C30 acylamino group, a C2-C30 alkoxycarbonylamino group, a C7-C30 aryloxycarbonylamino group, a C1-C30 sulfonylamino group, a sulfamoyl group, a C1-C30 alkylsulfamoyl group, a carbamoyl group, a C2-C30 alkylcarbamoyl group, a C1-C30 alkylthio group, a C6-C30 arylthio group, a C1-C30 heteroarylthio group, a C1-C30 alkylsulfonyl group, a C1-C30 alkylsulfinyl group, a ureido group, a C1-C30 alkylureido group, a C1-C30 phosphoric acid amino group, a hydroxy group, a mercapto group, a halogen atom, a halide, a cyano group, a sulfo group, a carboxyl group, a nitro group, a hydroxamic acid group, a sulfino group, a hydrazino group, an imino group, a C1-C30 heterocyclic group, a C3-C40 alkylsilyl group, a C2-C30 alkylphosphino group, triphenylsilyl and diphenylphosphino.

18. The organometallic complex of claim 17, wherein said CyC and said CyN are linked together to form a combined group selected from the group consisting of 2-phenylpyridine, benzothiazole, benzoxazole, 1-phenylpyrazole, 1-naphthylpyrazole, 5-(4-methoxyphenyl)pyrazole, 2,5-bisphenyl-1,3,4-oxadiazole, and 2,3-benzofuran-2-(4-biphenyl)-6-phenyl benzoxazole.

19. The organometallic complex of claim 17, wherein Y is substituted with at least one group selected from the group consisting of methyl, ethyl, isopropyl, t-butyl, n-octyl, n-decyl, n-hexadecyl, cyclopropyl, cyclopentyl, cyclohexyl, trifluoromethyl, vinyl, allyl, 2-butenyl, 3-pentyl, propargyl, 3-pentynyl, phenyl, p-methylphenyl, naphthyl, anthranyl, methylamino, dimethylamino, diethylamino, dibenzylamino, diphenylamino, ditolylamino, methoxy, ethoxy, butoxy, 2-ethylhexyloxy, phenyloxy, 1-naphthyloxy, 2-naphthyloxy, pyridyloxy, pyrazolyloxy, pyrimidyloxy, quinolyloxy, acetyl, benzoyl, formyl, pivaloyl, methoxycarbonyl, ethoxycarbonyl, phenyloxycarbonyl, acetoxy, benzoyloxy, acetylamino, benzoylamino, methoxycarbonylamino, phenyloxycarbonylamino, methanesulfonylamino, benzenesulfonylamino, methylsulfamoyl, dimethyl sulfamoyl, phenylsulfamoyl, methylcarbamoyl, diethylcarbamoyl, phenylcarbamoyl, methylthio, ethylthio, phenylthio, pyridylthio, 2-benzimidazolylthio, 2-benzoxazoylthio, 2-benzothiazolylthio, mesyl, tosyl, methanesulfonyl, benzenesulfonyl, methylureido, phenylureido, phosphoric acid amido, diethylphosphoric acid amido, phenyl phosphoric acid amido, fluorine, chlorine, bromine, iodine, trifluoromethyl, imidazolyl, pyridyl, quinolyl, furyl, thienyl, piperidyl, morpholino, benzoxazolyl, benzimidazolyl, benzothiazolyl, trimethylsilyl, triphenylsilyl, dimethylphosphino, and diphenylphosphino.

20. The organometallic complex of claim 17, wherein said organometallic complex is represented by Formula 2:

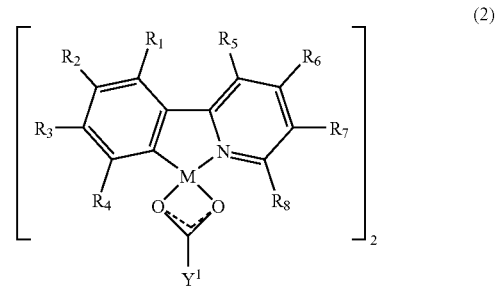

wherein M is selected from the group consisting of Ir, Pt, Rh and Pd;
$R_1$, $R_2$, $R_3$, $R_4$, $R_5$, $R_6$, $R_7$ and $R_8$ are independently selected from the group consisting of a hydrogen atom, a C1-C30 alkyl group, a C2-C30 alkenyl group, a halogen atom, a halide, an amino group, a hydroxy group, a mercapto group, a cyano group, a sulfonyl group and a sulfinyl group, and at least two adjacent groups of $R_1$ to $R_4$ and $R_5$ to $R_8$ can be interconnected to form a ring; and
Y' is a substituted or unsubstituted C2-C30 aryl group or a substituted or unsubstituted C2-C30 heteroaryl group, with the proviso that Y' is not pyridine, and the substituted C2-C30 aryl group or a substituted C2-C30 heteroaryl group of Y' is substituted with at least one group selected from the group consisting of a C1-C30 alkyl group, a halogenated C1-C30 alkyl group, a C2-C30 alkenyl group, a C2-C30 alkynyl group, a C6-C30 aryl group, an amino group, a C1-C30 alkylamino group, a C1-C30 alkoxy group, a C6-C30 aryloxy group, a C1-C30 heteroaryloxy group, a C1-C30 acyl group, a C2-C30 alkoxycarbonyl group, a C7-C30 aryloxycarbonyl group, a C2-C30 acyloxy group, a C2-C30 acylamino group, a C2-C30 alkoxycarbonylamino group, a C7-C30 aryloxycarbonylamino group, a C1-C30 sulfonylamino group, a sulfamoyl group, a C1-C30 alkylsulfamoyl group, a carbamoyl group, a C2-C30 alkylcarbamoyl group, a C1-C30 alkylthio group, a C6-C30 arylthio group, a C1-C30 heteroarylthio group, a C1-C30 alkylsulfonyl group, a C1-C30 alkylsulfinyl group, a ureido group, a C1-C30 alkylureido group, a C1-C30 phosphoric acid amino group, a hydroxy group, a mercapto group, a halogen atom, a halide, a cyano group, a sulfo group, a carboxyl group, a nitro group, a hydroxamic acid group, a sulfino group, a hydrazino group, an imino group, a C1-C30 heterocyclic group, a C3-C40 alkylsilyl group, and a C2-C30 alkylphosphino group.

* * * * *